United States Patent [19]

Kysilka et al.

[11] Patent Number: 4,467,204

[45] Date of Patent: Aug. 21, 1984

[54] APPARATUS AND METHOD FOR MEASURING OPTICALLY ACTIVE MATERIALS

[75] Inventors: James O. Kysilka, Moorhead, Minn.; Charles A. Sawicki, Fargo, N. Dak.

[73] Assignee: American Crystal Sugar Company, Moorhead, Minn.

[21] Appl. No.: 352,321

[22] Filed: Feb. 25, 1982

[51] Int. Cl.$^3$ ............................................. G01N 21/21
[52] U.S. Cl. .................................... 250/343; 356/368
[58] Field of Search ................ 250/343; 356/364, 366, 356/367, 368, 51

[56] References Cited

U.S. PATENT DOCUMENTS

| | | | |
|---|---|---|---|
| 2,766,652 | 10/1956 | Stanton | 356/367 |
| 3,283,645 | 11/1966 | Wada | 356/364 |
| 3,411,342 | 11/1968 | Liermann | 73/53 |
| 3,446,557 | 5/1969 | Wilkinson | 356/325 |
| 3,450,478 | 6/1969 | Sebestyen | 356/365 |
| 3,468,607 | 9/1969 | Sloane et al. | 356/73 |
| 3,471,240 | 10/1969 | Grosjean | 356/368 |
| 3,508,830 | 4/1970 | Hopkins et al. | 356/338 |
| 3,586,443 | 6/1971 | Hooper | 356/365 |
| 3,625,593 | 12/1971 | Taylor | 350/403 |
| 3,632,215 | 1/1972 | Holtz | 356/364 |
| 3,724,957 | 4/1973 | Tamate et al. | 356/367 |
| 3,803,384 | 4/1974 | Braunlich | 250/345 |
| 3,817,634 | 6/1974 | Barron et al. | 356/365 |
| 3,856,408 | 12/1979 | Hill et al. | 356/365 |
| 4,016,423 | 4/1977 | Meyer | 250/343 |
| 4,152,594 | 5/1979 | Schunck et al. | 250/343 |

FOREIGN PATENT DOCUMENTS 1698292 6/1973 Fed. Rep. of Germany .
30610 2/1981 Fed. Rep. of Germany .
2096764 of 0000 United Kingdom .

OTHER PUBLICATIONS

E. H. Korte and B. Schrader, "Polarimeter für den Infraroten Spektralbereich", *Messtechnik*, vol. 81, Dec. 1973, pp. 371-378, Fig. 2.

V. Ribarov, P. R. Kamadjiev, S. S. Sotirov, "Spectrometer Supplementary Apparatus for Measurement of Faraday Effect", *Comptes Rendus de l'Academie Bulgare des Sciences*, vol. 27, No. 10 (1974), pp. 1335-1337.

Primary Examiner—Janice A. Howell
Assistant Examiner—Constantine Hannaher
Attorney, Agent, or Firm—Merchant, Gould, Smith, Edell, Welter, and Schmidt

[57] ABSTRACT

A polarimeter system and method for sensing optical rotation caused by otically active materials in a solution are disclosed. The polarimeter system (10) includes a light source (11) for emitting infrared light, a polarizer (14) operatively connected to intercept the infrared light to produce a polarized beam therefrom and means for directing the beam through a sample of optically active material (15), which rotates the light beam. A beam splitting prism (16) splits the rotated polarized beam into its horizontal and vertical components. Infrared light detectors (17a) and (17b) convert the horizontal and vertical components into electrical signals representative of the optical rotation caused by the sample solution. Shaping circuitry (26) conditions the electrical signals for use by analog or digital (28) networks, that present the optical rotation or its physical correlative factor. Feedback circuitry (36) may be used to vary the light source (11) intensity in response to the detected light signals.

20 Claims, 9 Drawing Figures

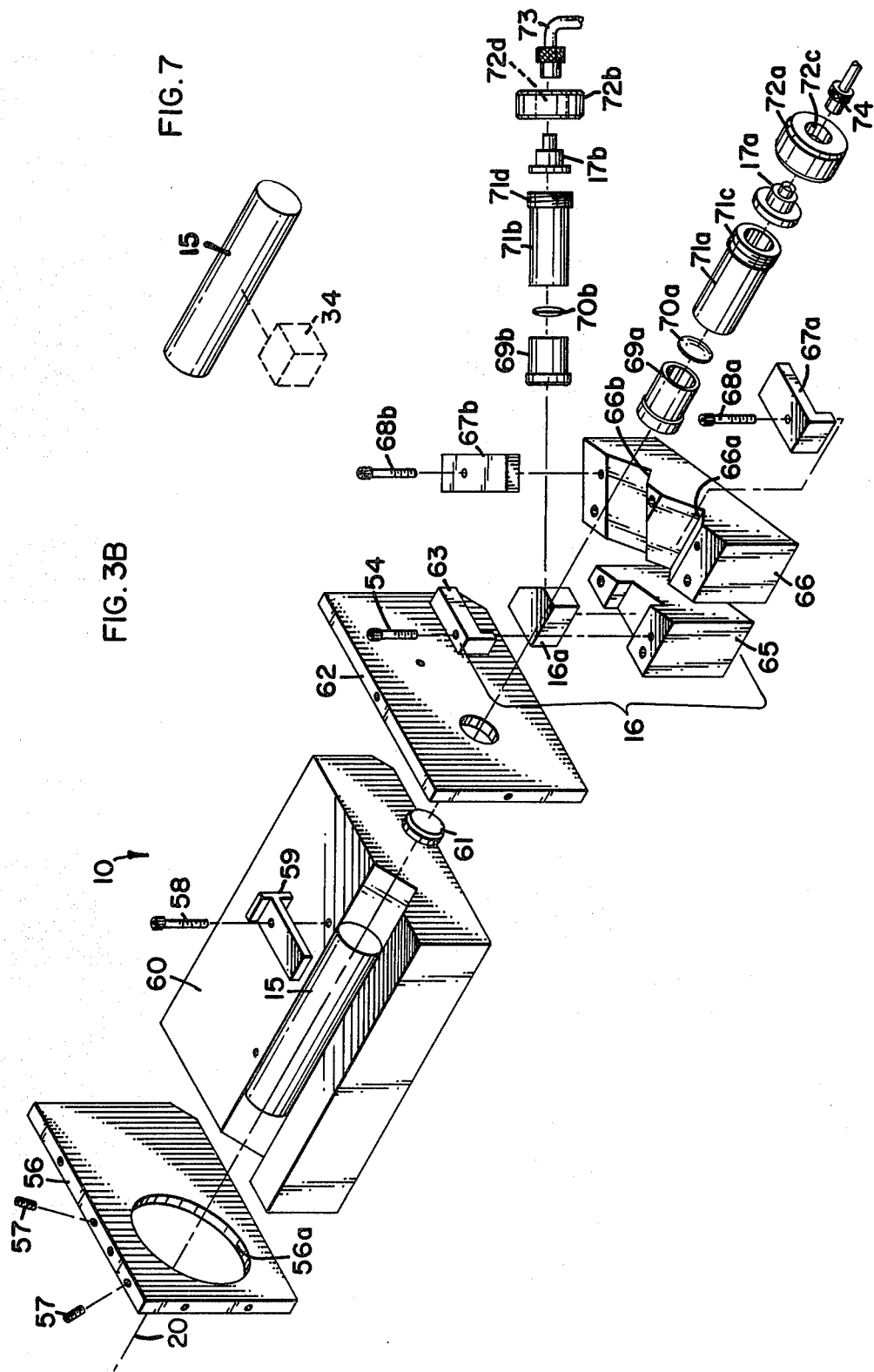

APPARATUS AND METHOD FOR MEASURING OPTICALLY ACTIVE MATERIALS

BACKGROUND OF THE INVENTION

1. Field of the Invention

This invention relates generally to an apparatus and method for measuring optically active materials. More particularly, this invention relates to an apparatus and method for measuring optically active materials, such as dark sugar solutions, that are highly absorbent at visible light wavelengths.

2. Description of the Prior Art

Certain solutions, e.g. sugar solutions, possess the property of being able to rotate the plane of vibration of polarized light. The degree of rotation of the plane of vibration per unit distance of the solution traversed by the polarized light varies in accordance with the strength of the solution. It is well known in the art to use a device having a light polarizer and an analyzer to measure the rotation of the plane of vibration of light passing through a solution, and to thereby determine the percent sugar content of the solution. One example of such an apparatus is shown in U.S. Pat. No. 3,411,342 issued to Theodore Liermann on Nov. 19, 1968. In the Liermann patent, the polarimeter consists of a mercury vapor lamp light source, a collimating lens, a primary polarizer to establish a reference point for measurement of optical rotation, a sample cell through which a continuous stream of crude syrup is circulated, and a measuring circuit that determines the extent of optical rotation caused by the sample and provides an appropriate output signal.

Such conventional polarimeters of the prior art have generally used "visible" light sources in the 500–633 nanometer wavelength emission range. Since dark sugar solutions, such as molasses, are highly absorbent at these wavelengths, it is virtually impossible to transmit a sufficient amount of visible light through such dark sugar solutions in order to measure their optical rotation. The prior art has addressed this problem by requiring clarification of the dark solutions, such as by the addition of lead subacetate $Pb(C_2H_3O_2)_2 \cdot 2Pb(OH)_2$. However, the use of lead subacetate as a clarifying agent to make the solution transparent at visible light wavelengths presents numerous problems in the health safety area, particularly in waste disposal. Use of such clarifying agents also create the possibility of error in the analysis since the addition of the clarifying agent may affect the true polarization rotation reading. Clarification also adds to the expense of testing the optically active material and increases the length of time required to perform the testing, thereby making such test methods unattractive to continuous flow-through testing operations such as would be present in a factory testing environment.

To date, there has been no known apparatus for measuring the optical rotation of dark sugar solutions, without requiring clarification of the solution before the rotation is measured.

The present invention addresses the problems associated with the prior art devices and methods which required pre-measurement clarification of the dark sugar solutions. The present invention provides a simple, accurate and inexpensive technique and apparatus for measuring the optical rotation of a dark sugar solution without requiring clarification of the sample solution. The present invention thus eliminates the concerns of waste disposal of toxic clarifying agent containing solutions, and is particularly suitable for measurement of continuous flow-through solutions such as found in factory environments.

SUMMARY OF THE INVENTION

The present invention includes an apparatus and method for measuring optically active materials. The invention utilizes a polarimeter system for sensing optical rotation caused by optically active material in solution. Sample containing means are used for containing a sample of the optically active material in a solution. A light source is energized to emit infrared light waves. A polarizer is operatively connected to intercept at least a portion of the infrared light emitted by the light source, to produce a polarized infrared light beam. Means for directing the polarized beam through at least a portion of the contained sample are provided. Detection means, operatively connected to intercept the polarized infrared light beam passing through the sample, are energized by the infrared beam and produce a signal or signals in response to the rotational condition of the polarized beam.

The present invention is particularly applicable to the measurement and analysis of optically active material such as dark sugar solutions, that are highly absorbent at visible light wavelengths but significantly less absorbent at infrared wavelengths. Since a dark sugar solution is more transparent at infrared wavelengths, with the present invention, there is no need to clarify the sugar solution sample being measured, such as by the addition of lead subacetate.

In a preferred embodiment of the invention, the polarimeter system further includes collimating optics connected to and positioned between the light source and the polarizer for collimating the infrared light. A band pass filter may also be positioned between the infrared light source and the polarizer, so that a predetermined wavelength of infrared light passes through the filter and polarizer and on through the sample.

In a preferred construction of the invention, the detection means produces first and second detected electrical signals corresponding respectively to the amount of polarized light intensity detected along horizontal and vertical polarization planes. The detected electrical signals are conditioned by electrical scaling circuitry for subsequent manipulation, analysis or use by either analog or digital circuitry. In a preferred configuration, digital circuitry in the form of a digital computer is employed to analyze the detected signals and to derive therefrom a determination of the percent of sugar content of a sample of sugar solution. In the preferred construction of the invention, the intensity of the light energy radiated by the infrared light source is regulated in response to the detected energy at any instant in time, such that the sum of the polarized light energy being detected by the pair of detection means remains constant.

The invention further comprises a method for determining the optical rotation caused by optically active material in a solution of the type wherein the material in solution is highly absorbent at visible light wavelengths, comprising the steps of: (a) polarizing light emitted from an infrared light source; (b) directing the polarized light through the optically active material; and (c) detecting the polarized infrared light after passing through the optically active material for determining the optical rotation of the polarized light beam caused by the optically active material. The invention further relates to such a method wherein the light from the infrared light source is transmitted through collimating optics prior to passing the light beam through the optically active material, and wherein the step of detecting the polarized light after passing through the optically active material is performed in part by splitting the polarized light into two orthogonal components.

While the present invention will be described with reference to a particular infrared light source, it will be understood that other types and configurations of infrared light sources may be employed within the spirit and intent of this invention. Further, while the preferred embodiment of the invention will be described with reference to specific electronic circuitry for analyzing the detected output signals by means of digital techniques, it will be understood that the invention applies equally well to evaluation and output circuitry that would employ analog techniques or digital techniques other than those specifically described. Further, while a particular detection scheme will be described with respect to the preferred embodiment of the invention, it will be understood that other detection schemes could equally well be employed within the spirit and intent of this invention.

BRIEF DESCRIPTION OF THE DRAWING

FIG. 3B is an exploded perspective view of the sample container and detector portions of the polarimeter system, of FIG. 2.

FIG. 7 is a perspective view of the sample cell of FIG. 3B.

DETAILED DESCRIPTION OF THE INVENTION

Figure 2:
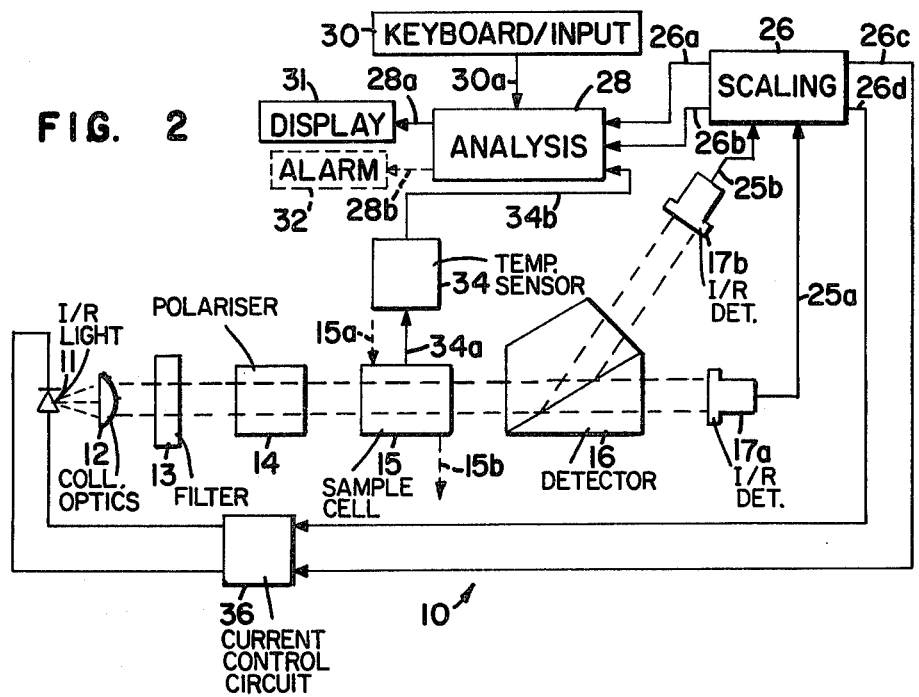
FIG. 2 is a schematic diagram illustration of a polarimeter apparatus constructed in accordance with the principles of the present invention.

Referring to the drawings, wherein like numerals represent like parts throughout the several views, there is generally illustrated at 10 of FIG. 2, a polarimeter system constructed according to the principles of this invention. The polarimeter system 10 has a light source 11 suitable for emitting light energy, when energized, in the infrared wavelength ranges. The infrared light source 11 may be an infrared light emitting diode, infrared laser diode or other suitable infrared light emitting source.

The polarimeter system further includes collimating optics generally designated at 12, and a polarizer 14. A band pass filter 13 may be included as illustrated in FIG. 2 to narrow the transmitted wavelength spectrum of the light source 11, depending on the type of light source used. As shown in FIG. 2, the infrared light source 11, collimating optics 12, band pass filter 13, and polarizer 14 are positioned in optical alignment about an axis 20, hereinafter described in more detail, such that the polarizer 14 intercepts at least a portion of the infrared light emitted by source 11, to produce a polarized beam of light. It is understood that the collimating optics 12, band pass filter 13, and polarizer 14 may be any suitable apparatus well-known in the industry. A preferred construction of these parts is illustrated in more detail in FIGS. 3A and 3B.

Figure 3A:
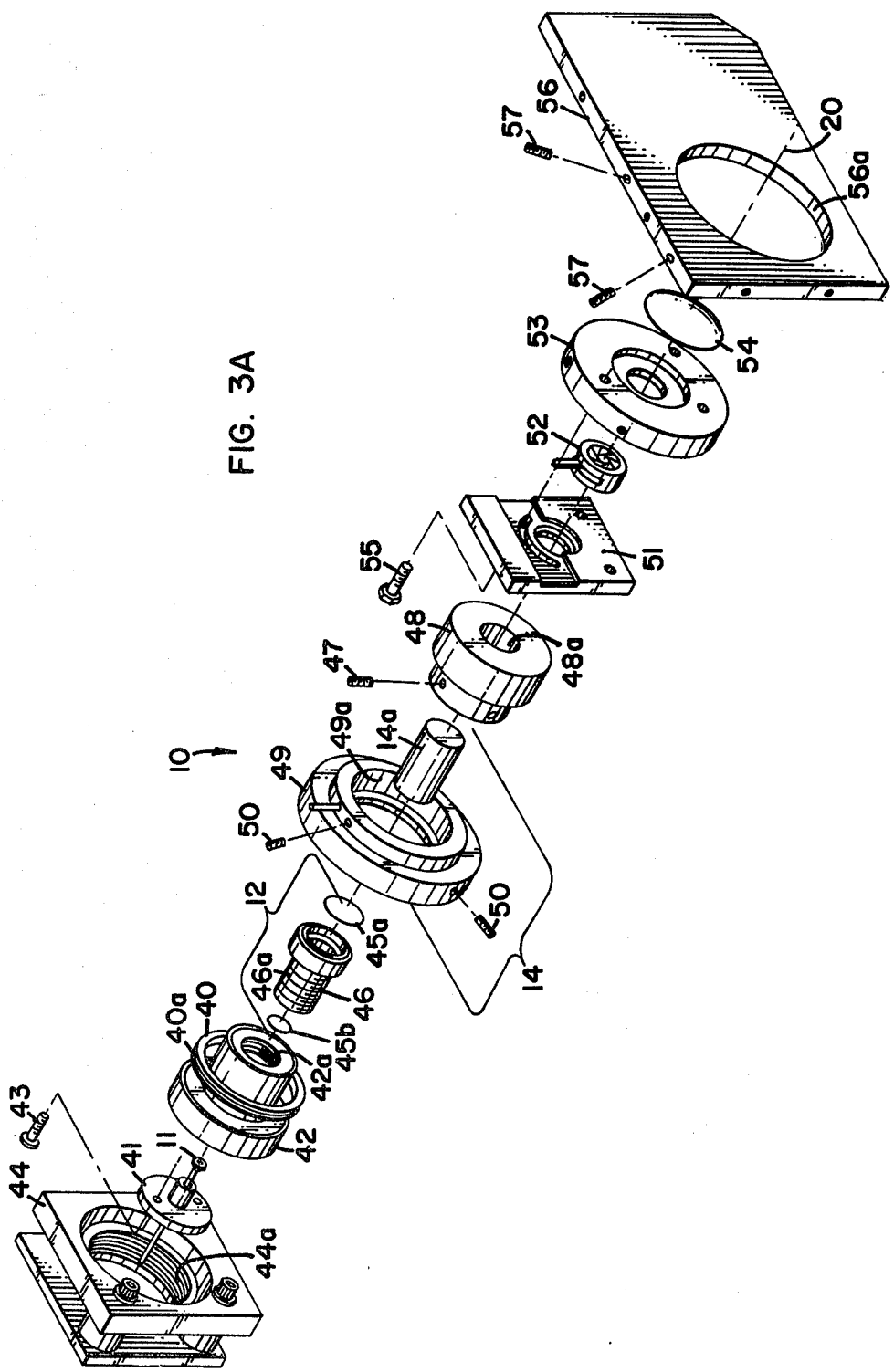
FIG. 3A is an exploded perspective view of a polarimeter apparatus illustrating the light source, collimating and directing and polarizing portions of the polarimeter system, of FIG. 2.

Referring to FIGS. 3A and 3B, which together from an exploded perspective view of the optical and detection portions of the polarimeter system 10 (shown without mounting plates), the infrared light emitting diode 11 is mounted to a diode holder 41. The diode holder 41 is mounted to a diode heat sink 42 by means of one or more screws 43. The heat sink 42 has an internally threaded bore 42a. Retaining ring 40 has a threaded exterior 40a for threading into the internally threaded bore 44a of a positioning mount 44, for securing the heat sink 42 into fixed coaxial position within the positioning mount 44, about the axis 20.

The collimating optics 12 includes a pair of lenses 45a and 45b and collimating lens holder 46. In the preferred embodiment construction, lens 45a is a DCX lens 18 mm × 39 mm FL from Edmund Scientific Company, Part No. 95247 and lens 45 is a DCX lens 9 mm × 11 mm FL, Edmund Scientific Company, Part. No. 94823. The collimating lens holder 46 has a threaded exterior portion 46a that threads into the threaded interior bore 42a of the diode heat sink 42, for mounting the lenses in coaxial alignment with the light source 11.

The polarimeter means 14 includes a polarizer 14a, polarizer rotator 49 and adapter 48. Polarizer 14a is coaxially positioned in the bore 48a of the polarizer adapter 48 and is held in the desired angular position by set screw 47. In a preferred embodiment, the polarizer 14a is a Karl Lambercht Model No. MGT25A10. The adapter 48 is coaxially mounted in the bore 49a within the polarizer rotator 49. The adapter 48 is secured in position by set screws 50.

An iris 52 and lens 54 are mounted in a lens and iris mount 53. An iris mount clamp 51 is connected to the lens and iris mount 53 by means of a plurality of screws 55, one of which is illustrated in FIG. 3A. The lens and iris mount 53 is mounted within circular opening 56a in lens bulk head 56 and is held in position by set screws 57. Lens 54 further collimates the beam.

Referring to FIG. 3B, which is an exploded extension of FIG. 3A, the lens bulk head 56 is again illustrated and a sample block 60 is positioned for mounting adjacent to the lens bulk head 56. A sample block clamp 59 and screw 58 position and hold a sample cell 15 on the sample block 60. A window bulk head 62 having a window 61 is positioned adjacent the sample block 60 with the window 61 coaxially aligned along the axis 20. Lens 54 and window 61 contain liquid that may spill from loading and unloading the sample cell 15 between the lens bulk head 56 and window bulk head 62.

The detector 16 includes a beam splitting prism polarizer 16a, prism mount 65 and prism mount clamp 63. The beam splitting prism polarizer 16a is positioned in optical alignment with the window 61 along the axis 20 and mounted on a prism mount 65 and held in position by prism mount clamp 63 and screw 54. A first infrared light detector 17a is positioned in a detector mount 72a. The mount 72a has a threaded inner bore 72c for mounting to a threaded exterior 71c of detector lens housing 71a. A detector lens 70a is positioned in detector retainer 69a. The detector retainer 69a mates with the detector lens housing 71a. This detector assembly is positioned in groove 66a of detector mount base 66 and is held in position by detector mounting clamp 67a and screw 68a.

A second infrared light detector 17b is positioned in a detector mount 72b. The mount 72b has a threaded inner bore 72d for mounting to a threaded exterior 71d of a detector lens housing 71b. Detector lens 70b is positioned in a detector retainer 69b. The detector retainer 69b mates with the detector lens housing 71b. This detector assembly is positioned in groove 66b of detector mount base 66 and is held in positioned by detector mounting clamp 67b and screw 68b. Detector lenses 70a and 70b collect the respective portions of the beam so that the beam falls on the active area of infrared light detectors 17a and 17b respectively. A 90° connector 73 is connected to the second detector 17b and a straight connector 74 is connected to the first detector 17a. The connectors 73 and 74 carry electrical signals from the detectors 17b and 17a respectively, as herein after described in more detail.

A sample cell 15 is provided for containing a sample of a dark sugar solution. While as shown in FIG. 7, the sample cell 15 is a three dimensional closed container and is for use in a batch type testing process, it is understood that the sample cell 15 may be modified to provide for continuous process testing. The flow of the dark sugar solution into and out of the sample cell 15 for continuous process testing is indicated by the dashed lines 15a and 15b in FIG. 2.

The polarized and collimated light beam is projected through the polarimeter system along the axis 20. The detector 16 is operatively connected to intercept the polarized infrared light beam passing through the sample container 15 and produces a signal or signals in response to the rotational condition of the polarized beam. In the preferred embodiment, the detector 16 includes a Karl Lambrecht Model Number SBT 210-45 analyzer beam splitting prism 16a. The beam splitting prism polarizer 16a separates the polarized light into its two components, one being referred to as the horizontal component and the other as the vertical component. Infrared light detectors 17a and 17b intercept, measure and convert the infrared light intensity of the horizontal and vertical polarized beams respectively into electrical signals. The infrared light detectors 17a and 17b may be photodiodes, photo-transistors, or photo-multipliers or any other suitable infrared light detectors.

Figure 1:
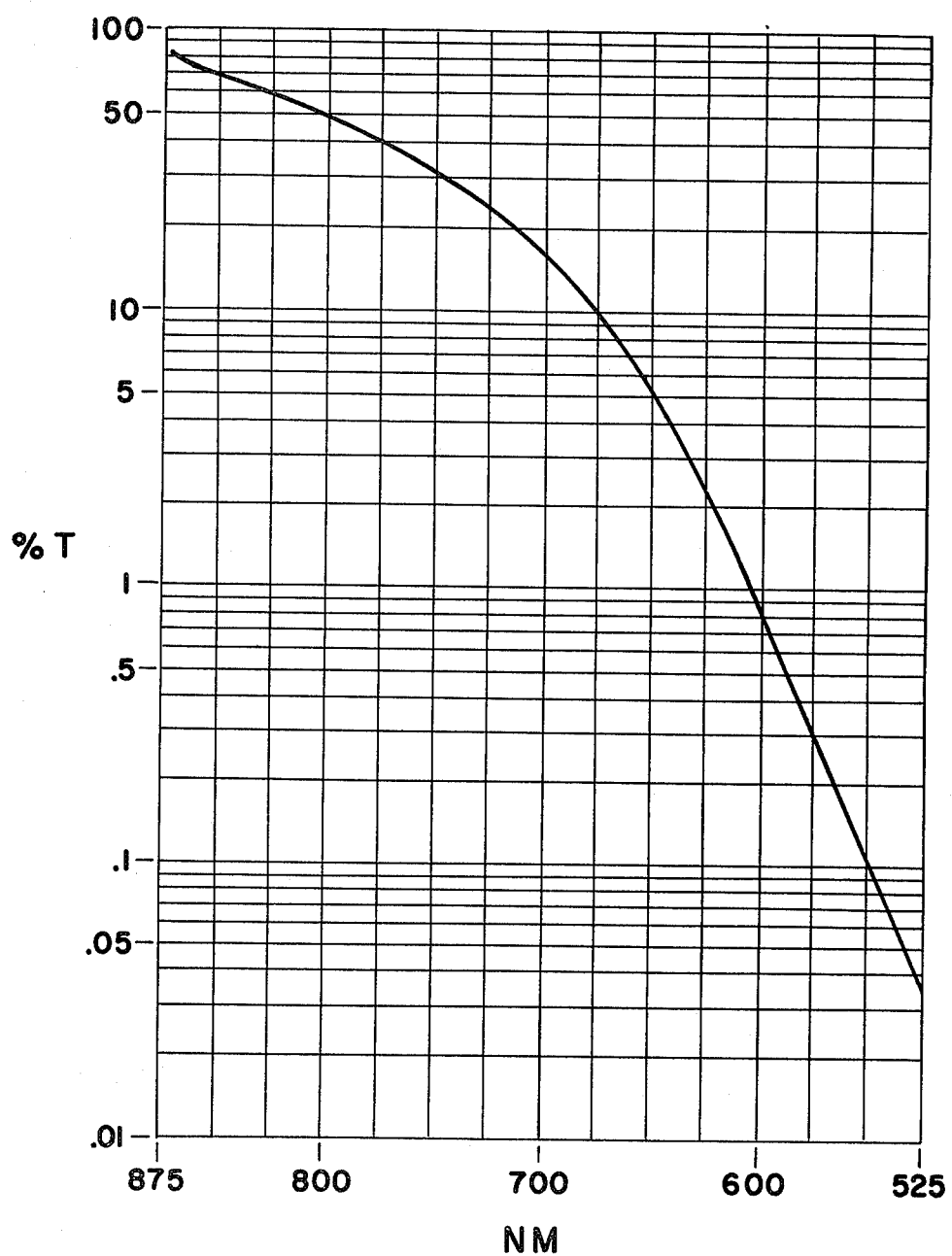
FIG. 1 is a graph illustrating the percent transparency of a typical dark sugar solution to light waves of various wavelengths.

FIG. 1 is a graph illustrating the transparency percentage of a beet sugar molasses (dark sugar) solution to various light wavelengths. As can be seen, the solution is only 0.3 percent transparent when subjected to light waves of 575 nanometers, 17 percent at 700 nanometers and approximately 80 percent at 875 nanometers. It can be seen that the molasses solution is from 1 to 3 orders of magnitude more transparent to the infrared wavelengths (700 nanometers and above) than to light in the 500 to 633 nanometer range (visible light). Other dark sugar solutions have similar light transparency properties. In a preferred embodiment, the infrared light source 11 emits light having a wavelength greater than or equal to 700 nanometers and preferably 875 nanometers or above.

In operation, a sample of the optically active material is placed in the sample container 15. Infrared light emitted from the infrared light source 11 is projected along the axis 20 through the collimating optics 12 and band pass filter 13 to the polarizer 14. The polarized beam from the polarizer 14 is directed toward and through the sample in the sample container 15. After passing through the sample, the polarized beam enters the detector 16 where it passes through the beam splitting prism 16a which splits the polarized light into its two components, one being horizontally polarized and the other vertically polarized.

The infrared light detectors 17a and 17b are respectively energized by the horizontally and vertically polarized signals and produce electrical signals proportional to the respective energy levels of the horizontal and vertical component light beams. The electrical signals can be processed by appropriate electrical or electronic apparatus to extract information therefrom as to the rotation angles of the beam as it passed through the solution sample. Such information can be correlated to the percentage of sugar content of the sample solution, can be used to generate other calculations or can be directly used to perform or regulate physical manipulations or operations (as for example, process control operations within a sugar-beet processing factory).

The post-detection portion of the apparatus, also referred to as the electronic portion of the apparatus, may use either analog or digital disciplines. In the preferred embodiment, such "electronic" portion of the apparatus is used for the purposes of measuring or calculating the percentage of sugar content of the solution contained within the sample container 15. Further, in the preferred embodiment, such computation or calculation is performed digitally, rather than through analog techniques. It will be understood, however, that the invention applies equally well to either digital or analog techniques and applies to any form of manipulation of the electrical signals derived from the detectors 17a and 17b, whether such manipulation be for obtaining a measurement or mathematical result or for performing or initiating the performance of a physical operation or command.

Operation of a typical electronic output section for the apparatus may be illustrated by reference to a specific electronic structure used in association with the preferred embodiment. Referring to FIG. 2, the electrical signals produced by the first detector 17a in response to the horizontal component of the polarized detected beam is carried by means of a signal flow path 25a to a Scaling electrical functional block 26. Similarly, the electrical signal produced by the second detector 17b corresponding to the vertical component of the polarized detected beam is carried by means of a signal flow path 25b to a second input of the Scaling block 26. It will be understood that the term "signal flow path" may refer to one or a plurality of actual electrical wires or conductors.

The Scaling function block 26 generally comprises one or a plurality of amplifier stages for conditioning the detected signals, so as to place the detected signals in proper format for subsequent manipulation or use by the digital or analog circuitry to which they will be applied. In the preferred embodiment, the conditioned signals from the Scaling functional block 26 are applied by means of a pair of signal flow paths 26a and 26b to first and second input terminals of an Analysis functional block 28. In a digital system, the Analysis functional block 28 may comprise a digital computer. In the preferred embodiment, the Analysis functional block 28 comprises a type TM 990 computer manufactured by Texas Instruments, hereinafter described in more detail.

To complete the broad description of the electronic output section of the preferred embodiment, referring to FIG. 2, the Analysis functional block 28 has a Keyboard/Input module 30 associated with it for providing communication between an operator and the Analysis circuit 28. The Keyboard 30 communicates with the Analysis 28 functional block by means of a signal flow path 30a. The Analysis functional block 28 communicates back to an operator or the outside environment by means of signal flow paths 28a and 28b respectively illustrated in FIG. 2 as communicating with a Display panel 31 and Alarm network 32. It will be understood that such output communication from the Analysis functional block 28 may otherwise be provided directly by means of one or more signal flow paths to the appropriate circuitry corresponding to the functions being performed by the Analysis functional block 28. In the preferred embodiment, the Analysis functional block 28 receives an additional sensed input signal by means of a signal flow path 34b from a temperature sensor 34 operatively connected with the sample container 15 by means of the signal flow path 34a, to sense the temperature of the solution contained within the sample container 15. The temperature sensing block 34 may represent any appropriate temperature sensing element (not specifically illustrated in the Drawing, see FIG. 7) capable of generating a detectable electrical output signal in response to a sensed temperature.

In the preferred construction of the output electronics circuitry, the digital computer comprising the Analysis functional block 28 performs the calculations for computing the percentage of sugar content of the sampled solution, in response to the sensed electrical input information received from the signal flow paths 26a, 26b and 34b. Any appropriate analytical technique can be employed for making such determination in response to the received detected digital information. In the preferred embodiment, information corresponding to and defining a non-linear curve representing percentage of sugar content concentrations for various polarization angular rotations, is stored within the memory of the Analysis computer 28. The respective detected signals from the detectors 17a and 17b is processed by the Scaling functional block 26 to provide digital information signals by means of the signal flow paths 26a and 26b which the Analysis computer 28 can correlate to specific points of the non-linear curve stored within its memory. In the preferred embodiment, such correlation is performed by the computer by a "least-squares fit" method. It will be understood, however, that any appropriate techniques could be employed for determining such correlation. When the appropriate correlation is attained within the Analysis computer 28, the computer will display the resultant "correlation/fit" information by means of the Display 31 or the Alarm 32, that represents the degree of rotation of the polarized infrared light beam. Such information may be displayed in any appropriate manner such as in degrees of optical rotation, as sugar degrees rotation, or as a percentage of sugar content of the solution. Such techniques will be readily understood by those skilled in the art.

Figure 4:
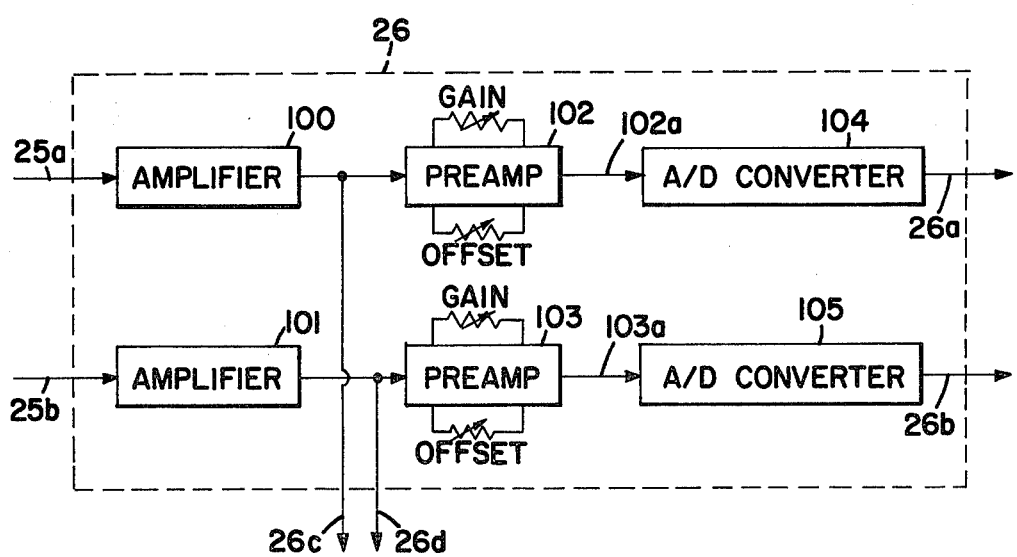
FIG. 4 is a block diagram representation of the scaling functional block illustrated in FIG. 2.

In the preferred embodiment, the detected signals from the detectors 17a and 17b are processed by means of the Scaling functional block 26 in the manner illustrated in FIG. 4. Referring thereto, the detected signals from the detectors 17a and 17b are illustrated as entering the Scaling functional block 26 by means of the signal flow paths 25a and 25b respectively, which apply such detected signals to a pair of amplifier stages respectively schematically identified at 100 and 101. The output signals respectively from the amplifier stages 100 and 101 are carried by means of the signal flow paths 26c and 26d through preamplifier stages 102 and 103 respectively to first and second A/D converter networks 104 and 105. Each of the preamplifier stages 102 and 103 is illustrated as having a "gain" and an "off-set" adjustment. The A/D converter networks are, in the preferred embodiment, 16-bit converter networks suitable for converting the applied analog input signals received thereby to a 16-bit digital output representation. The pair of 16-bit digital signals are carried by the signal flow paths 26a and 26b respectively to the Analysis computer 28 where they are used in the correlation determination.

Figure 5:
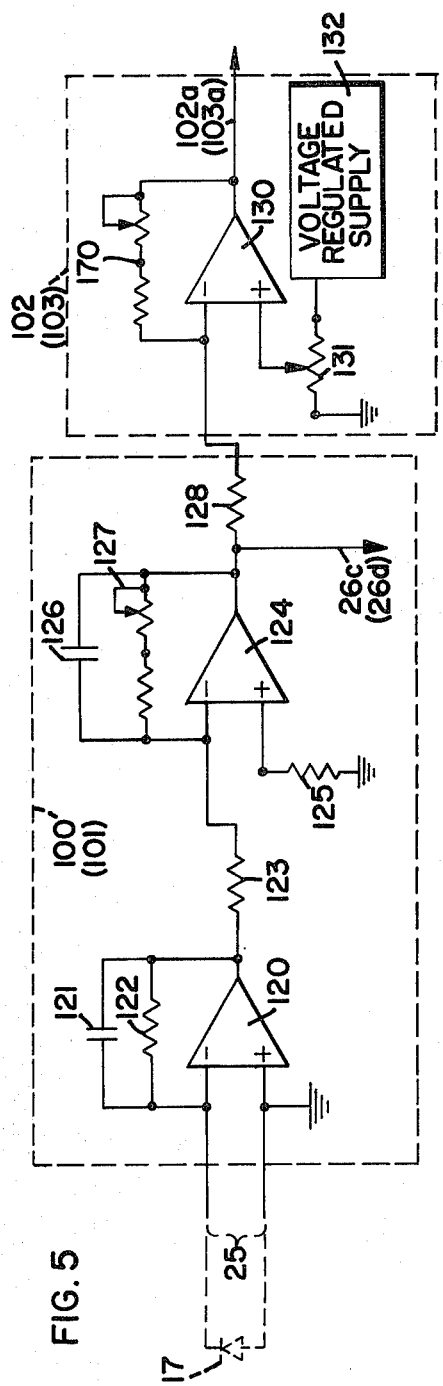
FIG. 5 is a schematic diagram illustrating a preferred circuit arrangement for the amplifier and preamplifier sections of the functional block diagram illustrated in FIG. 4.

In the preferred embodiment, the two channels of the Scaling functional block 26 are of generally like construction. The Amplifier 100 (101) and preamplifier 102 (103) portions of the scaling circuitry 26 are illustrated in more detail in FIG. 5, as they are constructed in the preferred embodiment. Referring thereto, the input signal flow path 25 is illustrated as a pair of input terminals respectively connected across the anode and cathode of one of the detector diodes 17. The anode of the detector diode 17 is connected to the non-inverting input terminal of a first amplifier 120 and is also connected to the common or reference voltage. The cathode of the detector diode is connected to the inverting input terminal of the amplifier 120. The feedback network of amplifier 120 comprises a capacitor 121 and a resistor 122 connected in parallel between the output and inverting input terminals of the amplifier 120. The output of amplifier 120 is connected by means of a resistor 123 to the inverting input of a second amplifier 124.

The non-inverting input terminal of amplifier 124 is connected by means of a resistor 125 to the reference potential. The feedback network of amplifier 124 comprises a capacitor 126 and a variable resistor 127 connected in parallel between the output terminal and inverting input terminal of the amplifier 124. The output signal from amplifier 124 provides the signal carried by signal flow path 26c or 26d, and also is applied by means of a resistor 128 to the inverting input terminal of an amplifier 130 of the preamplifier stage 102 (103).

The non-inverting input terminal of amplifier 130 is connected by means of a variable resistor 131 to the reference potential. The voltage level applied across resistor 131 is controlled by means of a regulated voltage supply, generally designated at 132. The feedback loop for amplifier 130 is provided by means of a variable resistor 170 connected between the output and inverting input terminals of amplifier 130. The output signal from amplifier 130 provides the analog signal excitation for the A/D converter 104 or 105 by means of the signal flow path 102a or 103a respectively. The variable resistance settings of the preamplifier 102 allow for "gain" and "off-set" adjustments, as is well-known in the amplifier art.

While a preferred configuration of the amplifier and preamplifier circuitry has been illustrated, it will be understood that other appropriate circuit configurations could be used to perform the desired scaling functions, within the spirit and scope of this invention.

Figure 6:
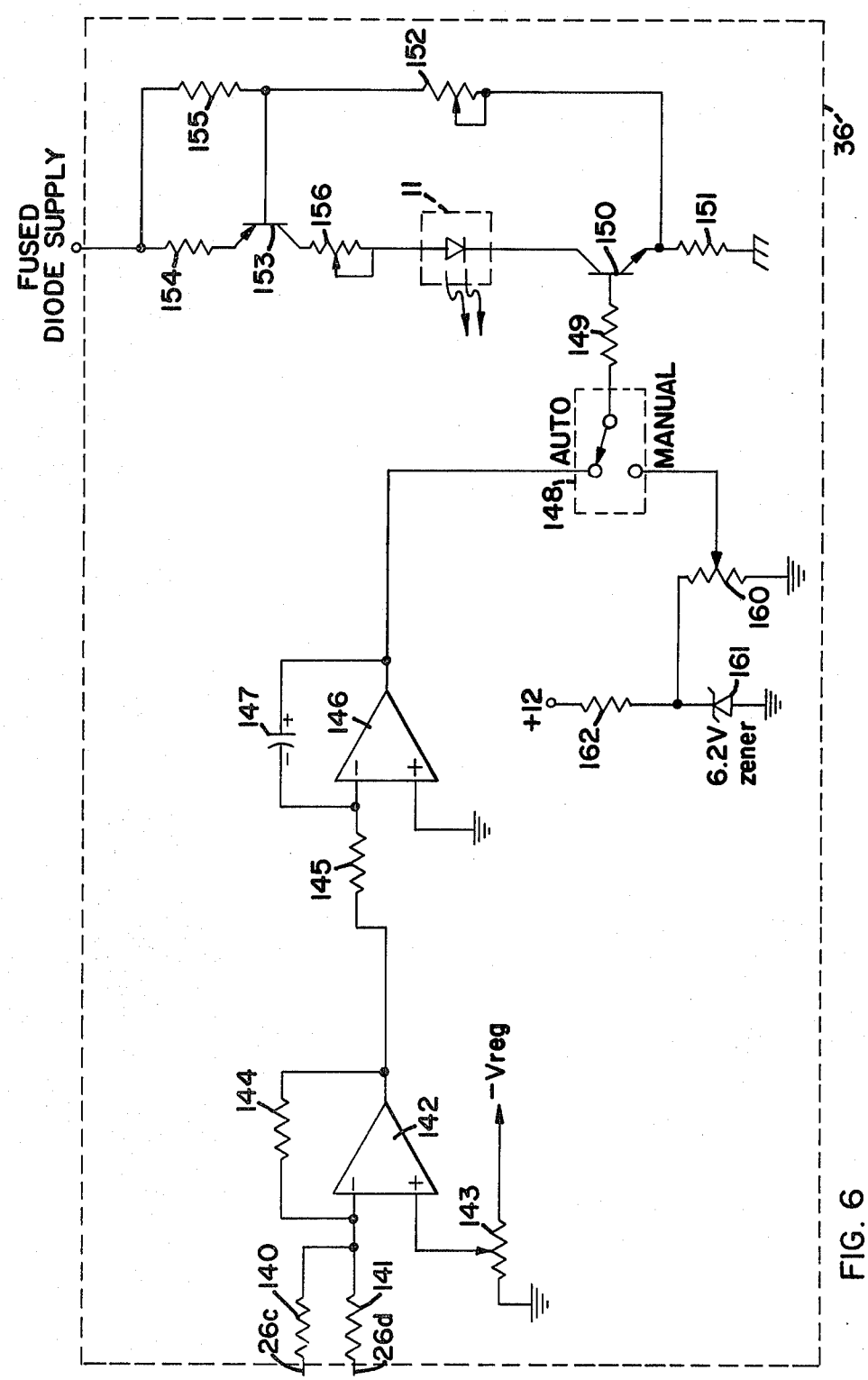
FIG. 6 is a schematic diagram of a preferred circuit configuration for implementation of the light intensity control circuit disclosed in FIG. 2.

Referring to FIGS. 2 and 4, the signals carried from the Scaling functional block 26 by means of the signal flow paths 26c and 26d are applied to a current control network, generally designated at 36. A preferred construction of the current control network 36 is illustrated in more detail in FIG. 6. Referring thereto, the signal flow paths 26c and 26d are respectively connected by means of resistors 140 and 141 to the inverting input terminal of an amplifier 142. The non-inverting input terminal of amplifier 142 is connected through a variable resistor 143 to the reference potential, and the voltage across resistor 143 is regulated by a regulated voltage source (not illustrated). A feedback resistor 144 is connected between the output terminal and the inverting input terminal of amplifier 142. Amplifier 142 acts as a comparator for the combined detected input signals applied by means of the signal flow paths 26c and 26d against the predetermined voltage established by resistor 143.

The output signal from amplifier 142 supplied by means of a resistor 145 to the inverting input terminal of an amplifier 146. The non-inverting input terminal of amplifier 146 is directly connected to the reference potential, and a feedback capacitor 147 is connected between the output and inverting input terminals of amplifier 146, making amplifier 146 operable to integrate the signal output from amplifier 142.

The output terminal of amplifier 146 is connected through a switch 148 and resistor 149 to the base of an npn transistor 150. The collector of transistor 150 is directly connected to the cathode of the infrared source diode 11, and the emitter of transistor 150 is connected through a current limiting resistor 151 to the reference potential.

The emitter of transistor 150 is also connected through a variable resistor 152 to the base of a pnp transistor 153. Transistor 153 further has an emitter connected through a resistor 154 to a fused voltage supply source, which source is also connected by means of a resistor 155 to the base of transistor 153. The collector of transistor 153 is connected by means of a variable resistor 156 to the anode of the infrared diode source 11. The transistor 153 and associated resistors function as a supply source of current for energizing the infrared diode 11, and the transistor 150 operates as a current driver circuit for regulating the current flow through diode 11 in response to the integrated drive signal from amplifier 146. Resistor 151 limits the maximum current that can be drawn through the source diode 11.

The switch 48 provides for manual (non-regulated) energization of the source diode 11. When the switch contact is positioned in the "manual" position, the base of transistor 150 is connected through the series combination of resistor 149, and a variable resistor 160 to the cathode of a zener diode 161. The anode of zener diode 161 is directly connected to the reference potential. The cathode of diode 161 is also connected by means of a resistor 162 to the positive supply potential. In the preferred embodiment, the zener diode 161 establishes a 6.2 volt regulated voltage level at its cathode.

The current control circuit 36 controls the current flow through the source diode 11 in response to the total intensity of polarized light detected by the detectors 17a and 17b. The regulation of source diode current is maintained at a level such that the detectors 17a and 17b always are exposed to the same "total" (i.e. sum of detected light intensity amounts) amount of light intensity, regardless of the absorption by the sampled solution. Such current control is, however, limited by the current flow capability of diode 11, by means of the current limiting resistor 150. Such light intensity compensates for any nonlinearities in the detectors 17a and 17b that may affect the detected readings of such devices. The light control regulator also permits operation of the light source at the lowest energy level possible that will still provide an adequate light level, to extend the operating life of the light source 11.

Figure 8:
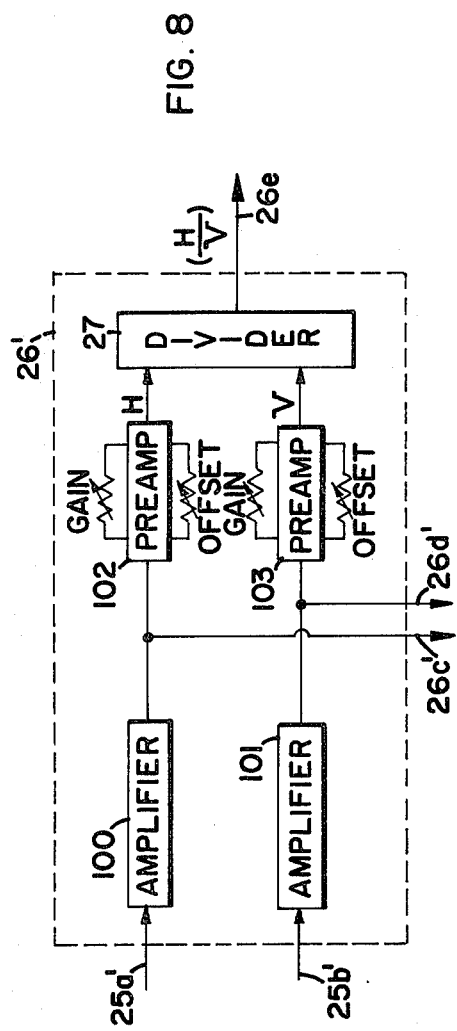
FIG. 8 is a block diagram respentation of an alternate configuration of the scaling functional block illustrated in FIG. 2.

An alternate configuration for the Scaling functional block 26, that could elminate the need or desirability for the Current Control network 36 is illustrated in FIG. 8. Referring thereto, like elements and components as previously described are identified by a "prime" (i.e.') designation. Signal flow from paths 25a' and 25b' passes through amplifiers 100, 101, 102 and 103 as previously described. However, instead of applying the output signals from preamplifiers 102 and 103 to A/D converters, such signals (designated as H and V) are applied to a Divider network 27 which forms the ratio (H/V) of the input signals. The ratio signal is then carried by means of the signal flow path 26e to the Analysis section 28. The advantage of forming a ratio is that intensity variations in the detected signals carried by paths 25a' and 25b' identically cancel one another in the (H/V) output signal.

While a particular electronic configuration and various circuits therefore have been illustrated for implementation of the invention, it will be readily apparent to those skilled in the art that many alternative circuits, configurations and analysis arrangements may be envisioned within the spirit and scope of this invention.

Similarly, other parameters such as the sensed temperature parameter generated by temperature sensor 34 may be used in the analysis of the particular solution sample. While temperature considerations for such analyzed samples are not generally relevant in laboratory situations, they may become particularly important in on-line (i.e. continuous flow-through) applications in factory situations wherein the sampling procedure may be exposed to severe temperature gradients under operative conditions.

Other modifications of the invention will be apparent to those skilled in the art in light of the foregoing description. This description is intended to provide specific examles of individual embodiments which clearly disclose the present invention. Accordingly, the invention is not limited to these embodiments or to the use of elements having specific configurations and shapes as presented herein. All alternative modifications and variations of the present invention which follows in the spirit and broad scope of the appended claims are included.

We claim:

1. A polarimeter system for sensing optical rotation caused by optically active material in a dark sugar solution, said polarimeter system comprising:
   (a) means for containing a liquid sample of optically active material in the dark sugar solution;
   (b) an infrared light source for emitting infrared light;
   (c) polarizer means operatively connected to intercept at least a portion of said infrared light for producing a polarized light beam therefrom;
   (d) means for directing said polarized light beam through at least a portion of said liquid sample; and (e) infrared light detection means operatively connected to intercept said light beam after passing through said liquid sample, for producing a signal in response to the rotational condition of said polarized light beam, whereby the optical rotation caused by the dark sugar solution may be determined.

2. The polarimeter system of claim 1, wherein the light emitted from said infrared light source has a wavelength equal to or greater than 700 nanometers.

3. The polarimeter system of claim 1, wherein the light emitted from said infrared light source has a wavelength equal to or greater than 875 nanometers.

4. The polarimeter system of claim 1, wherein said infrared light souce comprises an infrared laser diode.

5. The polarimeter system of claim 1, wherein said detection means comprises:
(a) means for splitting said polarized light beam after passing through said liquid sample into two components with orthogonal polarizations;
(b) means for receiving and sensing said components; and
(c) means for determining the ratio of one of said components to the other of said components.

6. The polarimeter system of claim 1, further comprising collimating optic means operatively connected between said light source and said containing means, for collimating at least a portion of said infrared light emitted by said light source.

7. The polarimeter system of claim 1, further comprising a band pass filter operatively connected between said light source and said polarizer means to intercept at least a portion of said infrared light, for passing, only a predetermined wavelength of said infrared light to said polarizing means.

8. The polarimeter system of claim 1, further comprising means for sensing the temperature of the optically active material and means for transmitting a signal responsive to the sensed temperature to said detection means.

9. The polarimeter system of claim 1, further comprising means for varying the intensity of said infrared light source in response to the light absorption property of said liquid sample.

10. A polarimeter system for sensing optical rotation caused by optically active material in a dark sugar solution, said polarimeter system comprising:
(a) means for containing a liquid sample of optically active material in the dark sugar solution;
(b) an infrared light source for emitting infrared light, the light emitted from said infrared light source having a wavelength equal to or greater that 700 nanometers;
(c) polarizer means operatively connected to intercept at least a portion of said infrared light for polarizing said portion of said infrared light to produce a polarized beam of said light;
(d) means for directing said polarized beam through at least a portion of said liquid sample;
(e) collimating optics operatively connected to and positioned between said light source and said containing means;
(f) a band pass filter operatively connected to and positioned between said light source and said polarizer means;
(g) detection means operatively connected to intercept said beam passing through said liquid sample for producing a signal in response to the rotational condition of said polarized beam; and
(h) means for varying the intensity of said infrared light source, in response to the amount of said polarized light beam being asorbed by said liquid sample, whereby the optical rotation caused by the dark sugar solution may be determined.

11. A polarimeter system for sensing optical rotation caused by a dark sugar solution without the need to clarify the dark sugar solution, said polarimeter system comprising:
(a) a sample container for holding a liquid sample of the dark sugar solution;
(b) an infrared light source for emitting infrared light;
(c) polarizer means operatively connected to intercept at least a portion of said infrared light for polarizing said portion of said infrared light to produce a polarized beam of said light;
(d) collimating optics operatively connected to and positioned between said light source and said polarizing means, whereby said infrared light is collimated;
(e) means for positioning said container in alignment with said infrared light source for intercepting said, polarized, collimated light beam wherein said polarized, collimated light beam passes through at least a portion of said sample container holding the dark sugar solution; and
(f) detection means operatively connected to intercept said beam passing through said liquid sample, producing a signal in response to the rotational condition of said polarized beam, whereby the optical rotation caused by the dark sugar solution may be determined.

12. The polarimeter system of claim 11, wherein the light emitted from said infrared light source has a wavelength equal to or greater than 700 nanometers.

13. The polarimeter system of claim 11, wherein said detection means comprises:
(a) means for splitting said polarized beam after passing through said liquid sample into two components with orthogonal polarizations;
(b) means for receiving and sensing said components and for producing sensed output signals in response thereto; and
(c) means for conditioning said sensed signals for processing by electrical networks.

14. The polarimeter system of claim 13, wherein said conditioning means includes means for determining ratio of one of said orthogonal components to the other of said orthogonal components.

15. The polarimeter system of claim 11, further comprising a band pass filter operatively connected to and positioned between said light source and said polarizer means, whereby only a predetermined wavelength of said infrared light passes through said filter to said polarizer means.

16. The polarimeter system of claim 11, further comprising means for measuring the temperature of the optically active material and means for transmitting the temperature measurement to said detection means.

17. A method for determining the optical rotation caused by optically active material in a liquid solution, such material in solution being characterized by being highly absorbent of visible light wavelengths, said method comprising:
(a) polarizing light emitted from an infrared light source;

(b) directing the polarized light through a sample of optically active material; and (c) detecting the polarized light after passing through the optically active material to determine the optical rotation caused by the optically active material in the liquid solution.

18. A method for determining the optical rotation caused by a dark sugar solution of the type that is highly absorbent to visible light wavelengths, said method comprising:

(a) producing infrared light waves;

(b) transmitting at least portion of said infrared light waves through collimating optics;

(c) polarizing said collimated light emitting from the collimating optics;

(d) directing said polarized light through a dark sugar solution; and (e) analyzing the optical rotation of the polarized infrared light after passing through said sugar solution, and caused by the sugar solution.

19. The method of claim 18, wherein the analyzing step includes detecting the polarized infrared light after passing through the sugar solution by splitting the polarized light into two components with orthogonal polarizations for use in determining optical rotation.

20. The method of claim 18, wherein the analyzing step includes the step of forming a ratio of the two orthogonal components.

* * * * *